United States Patent
Stensrud et al.

(12)

(10) Patent No.: US 10,947,208 B2
(45) Date of Patent: Mar. 16, 2021

(54) ORGANOTIN CATALYSTS IN ESTERIFICATION PROCESSES OF FURAN-2,5-DICARBOXYLIC ACID (FDCA)

(71) Applicants: Archer Daniels Midland Company, Decatur, IL (US); DUPONT INDUSTRIAL BIOSCIENCES USA, LLC, Wilmington, DE (US)

(72) Inventors: Kenneth Stensrud, Decatur, IL (US); Stuart Fergusson, Kingston (CA)

(73) Assignees: ARCHER DANIELS MIDLAND COMPANY, Decatur, IL (US); DUPONT INDUSTRIAL BIOSCIENCES USA, LLC, Wilmington, DE (US)

( * ) Notice: Subject to any disclaimer, the term of this patent is extended or adjusted under 35 U.S.C. 154(b) by 110 days.

(21) Appl. No.: 16/480,166

(22) PCT Filed: May 11, 2017

(86) PCT No.: PCT/US2017/032233
§ 371 (c)(1),
(2) Date: Jul. 23, 2019

(87) PCT Pub. No.: WO2018/093413
PCT Pub. Date: May 24, 2018

(65) Prior Publication Data
US 2020/0354329 A1    Nov. 12, 2020

(30) Foreign Application Priority Data
Nov. 17, 2016    (WO) ................ PCT/US2016/062491

(51) Int. Cl.
*C07D 307/68*    (2006.01)
*B01J 31/12*    (2006.01)

(52) U.S. Cl.
CPC .......... *C07D 307/68* (2013.01); *B01J 31/122* (2013.01); *B01J 2231/49* (2013.01); *B01J 2531/004* (2013.01)

(58) Field of Classification Search
CPC ... C07D 307/68; B01J 31/122; B01J 2231/49; B01J 2531/004
See application file for complete search history.

(56) References Cited

U.S. PATENT DOCUMENTS

| | | | |
|---|---|---|---|
| 4,950,746 A | 8/1990 | Navia | |
| 10,294,347 B2 | 5/2019 | Oshiro et al. | |
| 2012/0220507 A1 | 8/2012 | Grass et al. | |
| 2013/0171397 A1 | 7/2013 | Ghosh et al. | |
| 2014/0128623 A1 | 5/2014 | Janka et al. | |
| 2015/0307704 A1 | 10/2015 | Bhattacharjee et al. | |
| 2015/0315166 A1 | 11/2015 | Stensrud et al. | |
| 2016/0215119 A1 | 7/2016 | Wagner et al. | |
| 2018/0265629 A1* | 9/2018 | Bissell, II | C07D 307/68 |

FOREIGN PATENT DOCUMENTS

WO    2016/098496    6/2016

OTHER PUBLICATIONS

Office Action dated Sep. 28, 2020 in European Application No. 17 872 397.9.
Gubbels et al., "*Synthesis and Characterization of Novel Renewable Polyesters Based on 2,5-Furandicarboxylic Acid and 2,3-Butanediol*," Journal of Polymer Science Part A: Polymer Chemistry 51(4): 890-898, 2012, 9 pages.
Huang et al., "*Highly efficient metal salt catalyst for the esterification of biomass derived levulinic acid under microwave irradiation*," RSC Adv., 2016, 6, 2106-2111.
Wang et al., "*Toward the Rational Design of Galactosylated Glycoclusters That Target Pseudomonas aeruginosa Lectin A (LecA): Influence of Linker Arms That Lead to Low-Nanomolar Multivalent Ligands*," Chem. Eur. J. 2016, 22, 11785-11794.
International Search Report dated Nov. 6, 2017 in PCT/US2017/032233.
Written Opinion dated Nov. 6, 2017 in PCT/US2017/032233.
European Search Report dated Nov. 14, 2019 in European Application 17872397.9.

* cited by examiner

*Primary Examiner* — Timothy R Rozof
(74) *Attorney, Agent, or Firm* — Grüneberg and Myers PLLC

(57) ABSTRACT

A method for preparing sugar-based mono and diesters is described. The process entails the esterification of 2,5-furandicarboxylic acid (FDCA) with an alcohol in the presence of low loadings of a homogeneous organotin (IV) catalyst.

22 Claims, No Drawings

ORGANOTIN CATALYSTS IN ESTERIFICATION PROCESSES OF FURAN-2,5-DICARBOXYLIC ACID (FDCA)

CLAIM OF PRIORITY

This application is a National Stage entry under § 371 of International Application No. PCT/US2017/032233, filed on May 11, 2017, which claims the benefit of PCT International Application No, PCT/US2016/062491, filed on Nov. 17, 2016. International Application No. PCT/US2016/062491 claims the benefit of U.S. Provisional 62/259,124, filed Nov. 24, 2015.

FIELD OF INVENTION

The present disclosure pertains to processes for improving esterification of sugar-derived furan-2,5-dicarboxylic acid (FDCA). In particular, the invention involves methods for efficient preparation of derivatives of FDCA using organotin catalysts in Fischer-Speier esterification reactions.

BACKGROUND

Petroleum traditionally has been a primary source of raw material for making organic monomer precursors for common polymeric materials. However, with concerns about climate change and carbon dioxide emissions from fossil fuel sources, researchers have turned to bio-based, renewable carbon sources for plausible surrogate molecules. Carbohydrates, sometimes simply termed sugars, are a prodigious class of bio-based compounds that present a diverse array of extended, carbon-chained building blocks. For over 150 years, scientists have explored various chemical means for adapting the properties of sugars to an array of applications, including polymers. Dehydrative cyclization is a common transformation that sugars can undergo, particularly at elevated temperatures and in the presence of a catalyst, producing furan-based substances. For example, the common sugar, fructose, readily cyclizes at low pH to produce a versatile precursor, 5-hydroxymethyl-2-furfural, HMF. This process is illustrated in Scheme A.

Scheme A. Catalytic dehydrative cyclization of fructose to HMF

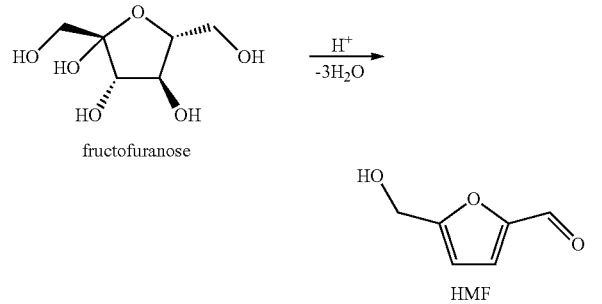

By virtue of its unique functionality, HMF can, in turn, be modified into other interesting molecular entities, such as furan-2,5-dimethanol (FDM), 2,5-bishydroxymethyl tetrahydrofuran (bHMTHF), diformylfuran (DFF), and 2,5-furandicarboxylic acid (FDCA). FDCA, in particular, has recently received considerable interest by myriad research groups as potentially renewable replacement for petro-based terephthalic acid in polymer applications.

Synthetic chemists have long sought to overcome challenges posed by the physical attributes of FDCA (e.g., its limited solubility in many common organic solvents and an extremely high melting point (>300° C.)). The high melting point of FDCA is a particular encumbrance when one desires to employ melt polymerization processes. Simple chemical modifications, such as esterification, often enables one to overcome barriers that arise from such physical properties. Esterification of FDCA with methanol to make dimethyl 2,5-furandicarboxylate (FDME) allows chemists to work with an appreciably more "manageable" derivative chemical compound that has a melting point at 112° C., and boiling point of 140-145° C. (10 torr), and facile solubility in a multitude of common organic solvents.

Over the years, esterification by autocatalysis has been demonstrated by several research groups in many publications. The inherent inefficiency of this process, however, arises from the need to use high temperatures and long, protracted reaction times to attain copacetic conversions of FDCA and yields of the target esters. This phenomenon of the esterification process has been a drawback which adds significantly to the cost of manufacture on an industrial or commercial scale operation. One conventional approach to enhance the esterification process has been to employ Brønsted acid catalysis, which on one hand greatly improves FDCA conversions and ester yields, but on another hand also readily drives alcohol condensation to undesired, low molecular weight ethers. This generation of byproducts can reduce the overall yield of desired ester product, and can encumber downstream processing, particularly relating to recycling and waste. Alternatively, Lewis acid catalysis in esterification have also been used, but Lewis acid catalysts often suffer from limited activity (lability), and a propensity to generate undesired Brønsted acids when in an aqueous matrix. In order to offset the specified hindrances of common esterification methods, alternate catalysts are needed.

SUMMARY OF INVENTION

The present disclosure describes, in part, a catalytic process for converting furan-2,5 dicarboxylic acid (FDCA) into monoalkylfuran-2,5-dicarboxylate (FDMAE) and dialkylfuran-2,5-dicarboxylate (FDAE), according to a reaction depicted in FIG. 1.

Scheme 1. Esterification of FDCA to FDMAE and FDAE

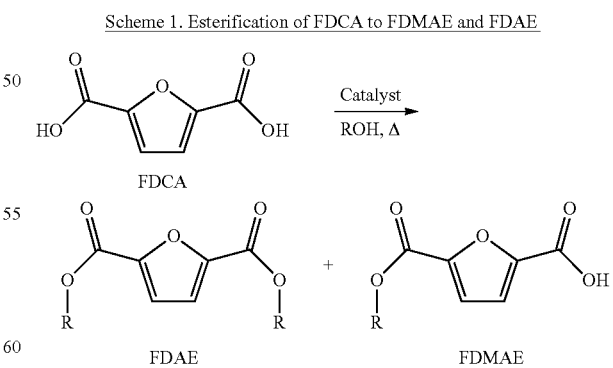

wherein the R-group is an aliphatic, having $C_1$-$C_{20}$ chain, or aromatic group, such as at least one of the following: alkyl, alkenyl, alkynyl, allyl, or aryl. In general, the process involves: reacting FDCA with at least an alcohol or a mixture of different alcohols in the presence of a homogeneous organotin acid catalyst for a time and temperature sufficient to fully esterify the FDCA and produce an intermediate mono- or di-ester; and removing any unreacted alcohol. The reaction can be in either an alcohol and/or diester solvent matrix. The process can generate relatively high conversions of FDCA and yields at reduced temperatures (e.g., 125° C.-225° C.) and at lower catalyst loadings (e.g., ≤1.0 mol. % relative to starting amount of FDCA) of the organotin catalysts. The tin ion in the organotin catalyst is Sn (IV), and has at least one tin-carbon covalent bond. The process can convert FDCA at least 85 mol. % to a mono- or di-ester. Furthermore, the organotin catalysts manifest markedly reduced side product activities relative to Brønsted acid counterparts in forming undesired alcohol condensations to ethers.

Additional features and advantages of the present synthesis method and material compounds will be disclosed in the following detailed description. It is understood that both the foregoing summary and the following detailed description and examples are merely representative of the invention, and are intended to provide an overview for understanding the invention as claimed.

DETAILED DESCRIPTION OF INVENTION

Section I. Description

The present disclosure describes, in part, a highly efficient process for preparation of mono- and di-esters of furan-2,5-dicarboxylic acid (FDCA). According to embodiments, the process involves plying homogeneous organotin catalysts to produce both the mono- and di-esters of FDCA from reactions with aliphatic and aromatic alcohols, such as ethanol, propanol, butanol, 2-ethylhexanol, phenol, benzyl alcohol, and 5-hydroxymethylfurfural (HMF). The process comprises: reacting FDCA with at least an alcohol or a mixture of different alcohols in either an alcohol or diester solvent matrix in the presence of a homogeneous organotin catalyst at a loading level of up to 5 or 10 mol. % for a reaction time and temperature sufficient to esterify said FDCA and produce a di-ester species at a FDCA conversion of at least 80 mol. %, and a di-ester yield of at least 5 mol. % greater than a comparable amount of Brønsted acid catalyst. The process produces less side products in amount of less than 0.05 mol. %, typically about 0.03-0.04 mol. %, and minimal to no decarboxylation.

Applicable homogeneous organotin catalysts as contemplated generally exhibit tin (IV) oxidation state, with an exception of tin (II) acetate. We have found unexpectedly that organotin catalysts having +4 oxidation state can be highly efficient for catalyzing the esterification reaction, with generation of minimal side products at reasonable reaction temperatures. The organotin catalyst can include at least one of the following: butylstannoic acid (BSA), dibutyltin oxide (DBTO), dibutyltin diacetate, butyltin tris 2-ethylhexanoate, dibutyltin maleate, dibutyltin dilaurate, dioctyltin oxide, dibutyltin bis(1-thioglyceride), dibutyltin dichloride, and monobutyltin dihydroxychloride. In certain particularly favored embodiments, the organotin catalyst can be selected from: butylstannoic acid, dibutyltin oxide, dibutyltin diacetate, butyltin tris 2-ethylhexanoate. Not necessarily limiting, the ligand complex surrounding the metal ion can have a cluster size with about 2-20 carbons, typically 2 or 4 to about 10 or 12 carbons, more typically about 2-8 carbons.

According to certain embodiments of the process the organotin catalyst loading level can be in a range from about 0.01 mo. % to about 5 mol. % (e.g., 2 mol. %, 3 mol. % or 4 mol. %). Typically, the catalyst loading level is in a range from about 0.05 mol. % to about 1.5 mol. %; more typically, the range is about 0.01 mol % to about 1 mol. %, preferably about 0.1 mol % to about 0.5 mol %.

Differentiated from heterogeneous catalysts, which are generally immobilized on carbon or aluminum scaffolds, homogeneous organometallic catalysts are monophasic with the reagents and can demonstrate advantages in catalyzing processes vis-à-vis supported metal catalyst species. One benefit of homogeneous catalysts over insoluble heterogeneous catalysts, particular to the application in the present method, is that the homogeneous species does not require filtration after use, which imparts improved economics, as an extra unit operation for such is avoided.

An advantageous feature of the current process with homogeneous organotin catalysis is that few side products are generated. This is a salient difference between the two kinds of catalysts. With the present organotin catalysts one can generate higher FDME yields than when using sulfuric acid (e.g., 93% vs. 87% respectively). Brønsted acids are significantly different and detrimental for producing more side-products, lower yields, and can trigger side reaction pathways—such as noticeable yields of dimethyl ether (DME) with Brønsted acid versus Lewis acid (2-3 orders of magnitude more). This effect has not been sufficiently recognized or appreciated. Conventionally, a sulfuric acid catalyst produces a great amount of DME, nearly 2 mol % in yield. Furthermore, in conventional processes, one uses catalyst in amounts that can be up to about 50 mol. % relative to the starting amount of FDCA. The tin catalysts generate significantly less, only about 0.03 mol. % yield of DME. In contrast for instance, strong Brønsted acid (e.g., HCl, $H_2SO_4$) catalyzed processes one effects significant amounts of flammable, gaseous alkyl and aryl ethers from alcohol condensations, which would need to perform extensive downstream separation or purification processing to remove both side products and the catalysts themselves before the product mixture could be used in synthesis of other or additional compounds. At such amounts, downstream processing will require catalyst removal.

Using the homogeneous organotin catalysts, the process can achieve a FDCA conversion of at least 3% or 5% greater, or a mono- or di-ester yield of at least 8 mol. % or 10 mol. % greater than a process reacted using a comparable amount of Brønsted acid catalyst. The homogeneous organotin catalyzed process enables the conversion of FDCA to the corresponding di-esters in reasonably high mole yields of at least 75 mol. %-82 mol. % (e.g., 77 mol. %, 80 mol. %), typically 85 mol. %-89 mol. % or greater. Typically, the molar yield ranges from about 85% or 87% to about 99%+, or any combination of ranges therein (e.g., 86%, 88%, 89%, 90%, 92%, 95%, 97%, 98%), depending on the reaction conditions (i.e., time, temperature pressure), and with the residue being the corresponding monoester. In particular examples, homogeneous organotin catalysts near quantitative conversions of FDCA to a furanic mono and diesters (e.g., 2,5-furandimethyl ester, FDME, when the alcohol is methanol) in yields near 90 mol. %. In certain embodiments, FDCA conversion is at least about 92 mol. %, 95 mol. % or 96 mol. %, or preferably about 99 mol. %. The yield of diester can be at least 50 mole %, typically about 70 mol. %-97 mol. %, more typically about 80 mol. % or 87 mol. % to about 90 mol. % or 95 mol. %.

A summary of results from catalyst screenings with methanol are summarized in Table 1.

TABLE 1

Data synopsis from catalyst screening of FDCA esterification in methanol

| Catalyst | Vendor/Product # | Product Name | FDCA conversion (mol %) | FDME yield (mol %) | Dimethyl ether yield (mol %, estimated from head space analysis) |
|---|---|---|---|---|---|
| Tin (IV) | | | | | |
| Butyltin tris-2-ethylhexanoate | PMC | FASCAT ®9102 | 99.61 ± 0.12 | 89.46 ± 1.15 | 0.0363 ± 0.0013 |
| Dibutyltin oxide | SIAL | | 99.72 ± 0.29 | 90.05 ± 1.34 | 0.0351 ± 0.0017 |
| Dibutyltin oxide | PMC | FASCAT ®4201 | 99.77 ± 0.28 | 90.47 ± 0.98 | 0.0362 ± 0.0029 |
| Dibutyltin diacetate | PMC | FASCAT ®4200 | 99.55 ± 0.17 | 90.09 ± 1.23 | 0.0349 ± 0.0022 |
| Butylstannoic acid | PMC | FASCAT ®9100 | 99.69 ± 0.08 | 91.21 ± 0.86 | 0.0334 ± 0.0021 |
| Dibutyltin oxide blend | FOMREZ | FOMREZ ®-SUL4 | 99.64 ± 0.11 | 89.04 ± 0.41 | 0.0343 ± 0.0013 |
| Dibutyltin oxide blend | FOMREZ | FOMREZ ® SUL-11 | 99.59 ± 0.19 | 87.08 ± 1.89 | 0.0336 ± 0.0011 |
| Dibutyltin dilaurate | PMC | FASCAT ®4202 | 99.06 ± 0.32 | 82.16 ± 0.97 | 0.0315 ± 0.0018 |
| Dibutyltin maleate | SIAL | | 99.19 ± 0.15 | 84.58 ± 0.86 | 0.0374 ± 0.0023 |
| Dibutyltin dichloride | PMC | FASCAT ®4201 | 99.26 ± 0.26 | 86.33 ± 1.16 | 1.1331 ± 0.0097 |
| Dioctyltin oxide | PMC | FASCAT ®8201 | 98.11 ± 0.29 | 76.12 ± 0.94 | 0.0335 ± 0.0027 |
| Monobutyltin dihydroxychloride | PMC | FASCAT ®4101 | 97.63 ± 0.10 | 80.15 ± 0.59 | 0.9126 ± 0.1073 |
| Tin dioxide | SIAL | | 95.91 ± 0.22 | 64.55 ± 0.70 | 0.0257 ± 0.0011 |
| Tin (II) | | | | | |
| Stannous octoate | PMC | FASCAT ® 2003 | 96.54 ± 0.12 | 69.68 ± 1.66 | 0.0332 ± 0.0021 |
| Stannous oxalate | PMC | FASCAT ® 2001 | 97.17 ± 0.07 | 78.74 ± 0.77 | 0.0295 ± 0.0029 |
| Tin acetate | SIAL | | 99.58 ± 0.16 | 88.99 ± 0.80 | 0.0526 ± 0.0014 |
| Tin chloride | PMC | FASCAT ®2004 | 94.11 ± 0.55 | 81.26 ± 1.69 | 0.9951 ± 0.1561 |
| Titanates | | | | | |
| Titanium tetrabutoxide | SIAL | TYZOR TBT | 98.57 ± 0.15 | 74.98 ± 1.65 | 0.0526 ± 0.0014 |
| Titanium tetraisopropoxide | SIAL | TYZOR TTIP | 98.31 ± 0.22 | 72.07 ± 0.89 | 0.0409 ± 0.0032 |
| Brønsted Acids | | | | | |
| Phosphonic | SIAL | | 97.42 ± 0.21 | 71.56 ± 1.15 | 0.1454 ± 0.0041 |
| p-Toluenesulfonic monohydrate | SIAL | | 95.16 ± 0.70 | 67.42 ± 1.43 | 0.0691 ± 0.0072 |
| Sulfuric | SIAL | | 99.49 ± 0.09 | 87.53 ± 1.23 | 1.6036 ± 0.1284 |
| Autocatalysis | | | 93.94 ± 1.47 | 64.26 ± 0.82 | 0.0367 ± 0.0020 |

When compared to standard catalyst loadings, the product tolerance for residual organometallic species is usually limited to aorganotin catalysts can be used in relatively low loads of about 10 mol. % or less, such as in amounts in a range of about 5 mol. % to 8 mol. % or less, relative to the starting amount of FDCA. Typically, the catalysts amount ranges from about 0.01 mol. % to about 2, 3 or 4 mol. %, desirably, about 0.05 to about 1.0 or 1.8 mol. %. This feature of the present reaction system enables one to allow the catalyst to remain in the product mixture without exigent need for removal, further simplifying downstream demand.

Esterification of FDCA can be conducted either in an inert atmosphere (e.g., nitrogen or argon) or in air without detrimental effect the reaction. In certain embodiments, the reaction temperature for the present process can be in a range from about 80° C. to about 275° C. Typically, the reaction temperature is in a range from about 100° C. to about 250° C.; more typically about 120° C.-245° C., preferably about 125° C. or 150° C. to about 225° C. or 230° C. (e.g., 140° C., 160° C., 215° C., 220° C.), more preferably about 175° C. or 180° C. to about 200° C. or 210° C. (e.g., 185° C., 195° C., 205° C., 208° C.). For instance, one can conduct the reaction in a Parr vessel of any material of composition (MOC) at a temperature in a range from about 125° C. to about 250° C., typically about 150° C. or 160° C. to about 225° C. or 235° C., more typically about 170° C. to about 200° C. (e.g., about 175° C. or 180° C. to about 190° C. or 195° C.).

The reaction time for the esterification process can be up to about 10 or 12 hours. Typically, the reaction time is in a range from about 10 minutes to about 8 hours; more typically, the reaction time is within about 3 or 4 hours, and desirably within about 1-2 hours until equilibrium. In certain embodiments the reaction can reach equilibrium within about 0.5 hours (i.e., 30 minutes) (e.g., 10, 15, 20 minutes). In an embodiment, for example, esterification can be performed within a 6 hour overall reaction time, typically within about 2 or 4 hours. More typically, the total reaction time ranges from about 1 or 2 hours to about 3 or 4 hours; particular durations can be about 0.5 to 1 hours or about 1-1.5 hours.

According to the process one can use either an alcohol solvent matrix and/or di-ester matrix is sufficient to dissolve the FDCA. The matrix can constitute about 50 wt. % to about 99 wt. % of alcohol and/or di-ester relative to an amount of FDCA. In other embodiments, the alcohol solvent matrix and/or di-ester solvent matrix can be at about 75 wt. % to about 97 wt. % relative to an amount of FDCA. The alcohols used for esterification of FDCA can be selected from various species, including either an aliphatic, having $C_1$-$C_{20}$ chain, or aromatic alcohol species, such as at least one of the following: alkyl, alkenyl, alkynyl, allyl, or aryl alcohols. Certain inexpensive and commonly used alcohol species, for example, may include: methanol, ethanol, propanol, isopropanol, n-butanol, sec-butanol, isobutanol, n-pentanol, 2-pentanol, 3-pentanol, n-hexanol, isohexanol, 2-ethylhexanol, cyclohexanol, heptanol, octanol, nonanol, decanol, phenol, benzyl alcohol, or 5-hydroxymethylfurfural.

Mono-ester products produced from the present process can include, for example:

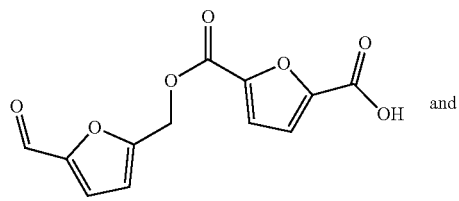

5-(((5-formylfuran-2-yl)methoxy)carbonyl)furan-2-carboxylic acid (FDCA-HMF)

and

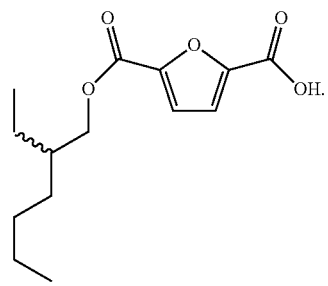

5-(((2-ethylhexyl)oxy)carbonyl)furan-2-carboxylic acid (FDCA-2EH)

Di-ester products made according to the present process may include, for example:

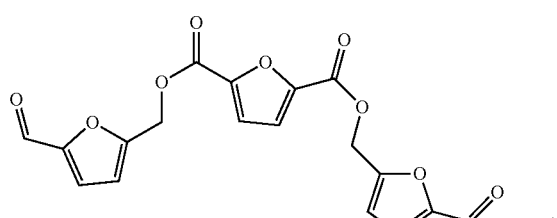

bis((5-formylfuran-2-yl)methyl)furan-2,5-dicarboxylate (FDCA-HMF)

and

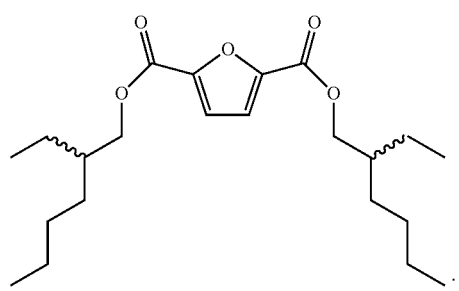

bis(2-ethylhexyl)furan-2,5-dicarboxylate (FDCA di(2EH))

Section II. Examples

In the following examples we further demonstrate the present method of preparing mono and dialkyl esters catalyzed by organotin species. For purpose of illustration the particular examples presented herein use methanol in the esterification, producing FDME and FDMME, but the process is not necessarily limited to such as other kinds of alcohols are also applicable.

A summary of are presented in the appended. In Tables 2-5, we summarize the additional examples of organotin catalysts and their efficacy in methanol and FDME solvents, respectively for esterification of FDCA to FDME at different concentrations, and under different catalyst loadings and operational conditions (i.e., time, temperature, pressure, etc.). Examples A, B, and C, respectively are at 17 wt. %, 26 wt. %, and 35 wt. % FCDA concentrations. Table 2 presents esterification reactions of FDCA in methanol solvent at 17 wt. % FDCA. In a first group, eight comparative examples are run without a catalyst; in a second group four examples are performed with an organotin catalyst loading of 0.1 mo. %, and six examples in a third group have an organotin catalyst loading of 0.5 mol. %. Generally, reactions with catalyst at temperatures between about 175° C. to about 250° C. were able to achieve near complete conversion of FCDA (i.e., ≥95 mol. %) and FDME yields of more than 85 mol. %.

Table 3 presents esterification reactions of FDCA in methanol solvent at 26 wt. % FDCA. In a first group six comparative examples are run without catalyst, and in a second group four examples have a catalyst loading of 0.5 mol. %. Even at lower temperatures (e.g., 175° C., 200° C.), the presence of the present organotin catalysts helps achieve better FDCA conversion (i.e., near complete) and FDME yield (e.g., ≥85 mol. %) than that produced at higher temperatures (e.g., 250° C.) without catalyst.

Table 4 presents esterification reactions of FDCA in methanol solvent at 35 wt. % FDCA. In a first group four comparative examples are run without catalyst, and in a second group four examples have a catalyst loading of 0.5 mol. %. Similar to the results in Table 3, the catalyzed reactions performed better than reactions without catalyst; one can achieve about 5 mol. % more FDME yield at reaction temperatures of about 200° C. or higher. This additional yield can be a significant benefit in industrial production.

Table 5 presents esterification of FDCA in FDME solvent. In the examples using the present organotin catalysts one can achieve similar or better conversion of FDCA, and a significant improvement in FDME yield over examples without catalyst. In some examples, the difference in FDME yield is at least 5 mol. %, others ≥10 mol. % or 12 mol. %.

Tables: Batch Esterifications of FDCA to FDME

I.

TABLE 2

Esterification of FDCA in methanol solvent Example A.
17 wt. % FDCA (6 g FDCA + 30 g MeOH)

| Catalyst Load (mol. %) | Rxn Temp (° C.) | Operating Pressure (psi) | Rxn Time (min) | Approximate Time to Equilibrium (min) | FDCA conversion | FDME yield (mol %) | Decarboxylation |
|---|---|---|---|---|---|---|---|
| None | 125 | 84   | 90  | —      | 21.59          | 1.60            | N |
| None | 150 | 170  | 90  | —      | 71.99          | 21.90           | N |
| None | 175 | 325  | 120 | —      | 89.82 ± 0.33   | 46.06 ± 1.14    | N |
| None | 185 | 360  | 180 | —      | 98.58          | 73.82           | N |
| None | 200 | 500  | 90  | —      | 95.80          | 61.10           | N |
| None | 210 | 590  | 150 | 135    | 98.86 ± 0.02   | 80.17 ± 1.03    | N |
| None | 225 | 750  | 90  | —      | 98.78 ± 0.03   | 77.35 ± 1.50    | N |
| None | 250 | 1100 | 90  | 30     | 99.09          | 82.59           | Y |
| 0.1  | 150 | 165  | 90  | —      | 79.18          | 28.30           | N |
| 0.1  | 175 | 325  | 90  | —      | 97.21          | 77.47           | N |
| 0.1  | 200 | 500  | 90  | 60     | 99.46          | 85.20           | N |
| 0.1  | 225 | 750  | 90  | 30     | 99.40 ± 0.23   | 85.61 ± 1.26    | N |
| 0.5  | 125 | 84   | 90  | —      | 40.71          | 4.98            | N |
| 0.5  | 150 | 175  | 90  | —      | 95.87          | 67.70           | N |
| 0.5  | 175 | 325  | 150 | 120    | 99.54 ± 0.18   | 88.49 ± 0.54    | N |
| 0.5  | 200 | 500  | 60  | 15     | 99.60 ± 0.31   | 88.98 ± 2.07    | N |
| 0.5  | 225 | 725  | 60  | Heat up | 99.63 ± 0.17  | 88.76 ± 1.33    | N |
| 0.5  | 250 | 1100 | 60  | Heat up | 99.54 ± 0.13  | 88.36 ± 1.98    | Y |

TABLE 3

Example B.
26 wt. % FDCA (10 g FDCA + 29 g MeOH)

| Catalyst Load (mol %) | Rxn Temp (° C.) | Operating Pressure (psi) | Rxn Time (min) | Approximate Time to Equilibrium (min) | FDCA conversion (mol %) | FDME yield (mol %) | Decarboxylation |
|---|---|---|---|---|---|---|---|
| None | 175 | 325  | 90  | —       | 87.95          | 48.45          | N |
| None | 185 | 336  | 180 | —       | 98.87          | 75.70          | N |
| None | 200 | 445  | 90  | —       | 95.72          | 65.65          | N |
| None | 210 | 590  | 150 | 150     | 98.88          | 80.16          | N |
| None | 225 | 745  | 90  | —       | 98.35          | 73.59          | N |
| None | 250 | 1045 | 60  | 45      | 99.03          | 80.89          | Y |
| 0.5  | 175 | 310  | 120 | —       | 99.67          | 87.52          | N |
| 0.5  | 200 | 475  | 90  | 30      | 99.52 ± 0.08   | 87.98 ± 0.61   | N |
| 0.5  | 225 | 735  | 60  | 15      | 99.62 ± 0.17   | 87.85 ± 0.57   | N |
| 0.5  | 250 | 1030 | 60  | Heat up | 99.57 ± 0.14   | 87.54 ± 1.92   | Y |

TABLE 4

Example C.
35 wt. % FDCA (15 g FDCA + 28 g MeOH)

| Catalyst | Rxn Temp (° C.) | Operating Pressure (psi) | Rxn Time (min) | Approximate Time to Equilibrium (min) | FDCA conversion (mol %) | FDME yield (mol %) | Decarboxylation |
|---|---|---|---|---|---|---|---|
| None      | 175 | 230 | 240 | —      | 80.16 | 37.79 | N |
| None      | 200 | 400 | 240 | —      | 98.47 | 78.01 | N |
| None      | 225 | 600 | 180 | —      | 98.19 | 77.30 | N |
| None      | 250 | 920 | 60  | —      | 98.73 | 77.65 | Y |
| 0.5 mol % | 175 | 236 | 90  | —      | 98.32 | 77.69 | N |
| 0.5 mol % | 200 | 395 | 90  | 90     | 99.08 | 83.95 | N |
| 0.5 mol % | 225 | 600 | 60  | 30     | 99.12 | 83.99 | N |
| 0.5 mol % | 250 | 925 | 60  | Heatup | 99.10 | 83.31 | Y |

II.

TABLE 5

Esterification of FDCA in FDME solvent

| Trial set | Catalyst | Temp (° C.) | P (psi) | MeOH (eq.) | Time (min) | Equilib. | FDCA conv. (mole %) | FDMME yld. (mole %) | FDME yld. (mole %) |
|---|---|---|---|---|---|---|---|---|---|
| 1 | Y | 170 | 83 | 2 | 45 | N | 67 | 56 | 12 |
| 2 | Y | 170 | 103 | 4 | 60 | N | 95 | 67 | 28 |
| 3 | Y | 170 | 140 | 8 | 60 | N | 97 | 54 | 43 |
| 4 | Y | 170 | 174 | 12 | 60 | N | 98 | 48 | 50 |
| 5 | Y | 180 | 109 | 4 | 60 | N | 96 | 65 | 31 |
| 6 | Y | 180 | 144 | 8 | 60 | N | 97 | 52 | 45 |
| 7 | Y | 180 | 209 | 12 | 60 | N | 98 | 44 | 54 |
| 8 | N | 180 | 121 | 4 | 60 | N | 79 | 66 | 13 |
| 9 | N | 180 | 155 | 8 | 60 | N | 85 | 67 | 18 |
| 10 | N | 180 | 211 | 12 | 60 | N | 89 | 67 | 22 |
| 11 | Y | 200 | 115 | 4 | 150 | Y (90 min) | 97 | 58 | 39 |
| 12 | Y | 200 | 179 | 8 | 150 | Y (45 min) | 99 | 36 | 63 |
| 13 | Y | 200 | 301 | 12 | 60 | Y (30 min) | 99 | 34 | 65 |
| 14 | N | 200 | 112 | 4 | 60 | N | 94 | 74 | 20 |
| 15 | N | 200 | 185 | 8 | 60 | N | 96 | 63 | 33 |
| 16 | N | 200 | 297 | 12 | 60 | N | 97 | 60 | 37 |
| 17 | Y | 220 | 135 | 4 | 150 | Y (30 min) | 97 | 58 | 39 |
| 18 | Y | 220 | 220 | 8 | 45 | Y (15 min) | 99 | 36 | 63 |
| 19 | Y | 220 | 375 | 12 | 60 | Y (15 min) | 99 | 34 | 65 |
| 20 | N | 220 | 134 | 4 | 150 | Y (30 min) | 96 | 74 | 23 |
| 21 | N | 220 | 221 | 8 | 45 | Y (45 min) | 98 | 61 | 37 |
| 22 | N | 220 | 379 | 12 | 60 | Y (30 min) | 98 | 54 | 44 |

I. Highly Effective Catalysts
A. Methanol Solvent

1) Butylstannoic Acid Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of butylstannoic acid (FASCAT®9100). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 0.6 mole % FDCA, 8.2 mole % FDMME, 91.2 mole % FDME, 0.03 mole % DME. No decarboxylation products, MF and FA, were descried.

2) Dibutyltin Oxide Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of dibutyltin oxide (FASCAT®9201). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 0.5 mole % FDCA, 9.0 mole % FDMME, 90.5 mole % FDME, 0.04 mole % DME. No decarboxylation products, MF and FA, were descried.

3) Dibutyltin Diacetate Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of dibutyltin diacetate (FASCAT®4200). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 0.6 mole % FDCA, 9.1 mole % FDMME, 90.4 mole % FDME, 0.04 mole % DME. No decarboxylation products, MF and FA, were descried.

4) Butyltin tris 2-ethylhexanoate Catalyzed Esterification of FDCA to FDME and FDMME Experimental: A 75 cc 316SS Parr vessels, each equipped with a glass enclosed magnetic stir bar, was charged with 10 g of FDCA (0.064 mol), 40 g of methanol (1.25 mol), and 50 mg of butyltin tris 2-ethylhexanoate (FASCAT®9102). While stirring at 875 rpm, the suspension was heated to 200° C. for 60 minutes, including a 60 minute heat up requirement. After this time, the reaction was quickly quenched by immersion of the vessel in an ice bath. The solid residual material was dried and analyzed (UPLC-PDA). The compositional analysis was as follows: 0.6 mole % FDCA, 9.3 mole % FDMME, 90.4 mole % FDME, 0.05 mole % DME. No decarboxylation products, MF and FA, were descried.

5) Comparative Example: No Catalyst Added

Experimental: A 75 cc 316SS Parr vessels, each equipped with a glass enclosed magnetic stir bar, was charged with 10 g of FDCA (0.064 mol), 40 g of methanol (1.25 mol), While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 6.1 mole % FDCA, 38.5 mole % FDMME, 55.4 mole % FDME, DME 0.01 mole %. No decarboxylation products, MF and FA, were descried.

B. Highly Effective Catalysts in FDME Solvent, 8 Mole Equivalents Methanol

1) Butylstannoic Acid Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 30 g of FDME, 16.4 g of methanol and 50 mg of butylstannoic acid (FASCAT®9100). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 1.1 mole % FDCA, 36.1 mole % FDMME, 62.8 mole % FDME, 0.04 mole % DME. No decarboxylation products, MF and FA, were descried.

2) Dibutyltin Oxide Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 30 g FDME, 16.4 g of methanol and 50 mg of dibutyltin oxide (FASCAT® 9201). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 1.5 mole % FDCA, 36.5 mole % FDMME, 62.0 mole % FDME, 0.06 mole % DME. No decarboxylation products, MF and FA, were descried.

3) Comparative Example, No Added Catalyst

Experimental: A 75 cc 316SS Parr vessels, each equipped with a glass enclosed magnetic stir bar, was charged with 10 g of FDCA (0.064 mol), 30 g of FDME, and 16.4 g of methanol. While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 3.5 mole % FDCA, 63.5 mole % FDMME, 33.0 mole % FDME, 0.04 mole % DME. No decarboxylation products, MF and FA, were descried.

II. Moderately Effective Catalysts

A. Methanol Solvent

1) Dibutyltin Maleate Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of dibutyltin maleate (Sigma Aldrich). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 0.7 mole % FDCA, 10.4 mole % FDMME, 88.9 mole % FDME, 0.04 mole % DME. No decarboxylation products, MF and FA, were descried.

2) Dibutyltin Dilaurate Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of dibutyltin dilaurate (FASCAT® 4202). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 0.6 mole % FDCA, 10.6 mole % FDMME, 88.8 mole % FDME, 0.07 mole % DME. No decarboxylation products, MF and FA, were descried.

3) Stannous (II) Acetate Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of stannous acetate (Sigma Aldrich). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 0.8 mole % FDCA, 11.2 mole % FDMME, 88.0 mole % FDME, 0.05 mole % DME. No decarboxylation products, MF and FA, were descried.

4) Dioctyltin Oxide Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of dioctyltin oxide (FASCAT® 8201). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 0.9 mole % FDCA, 12.6 mole % FDMME, 86.5 mole % FDME, 0.07 mole % DME. No decarboxylation products, MF and FA, were descried.

5) Dibutyltin Bis(1-thioglyceride) Catalyzed Esterification of FDCA to FDME and FDMME Experimental: A 75 cc 316SS Parr vessels, each equipped with a glass enclosed magnetic stir bar, was charged with 10 g of FDCA (0.064 mol), 40 g of methanol (1.25 mol), and 50 mg of dioctyltin oxide (FASCAT® 4224). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 1.1 mole % FDCA, 13.8 mole % FDMME, 85.1 mole % FDME, 0.03 mole % DME. No decarboxylation products, MF and FA, were descried.

B. FDME Solvent, 8 Mole Equivalents Methanol

1) Dibutyltin Dilaurate Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 30 g of FDME, 16.4 g of methanol (1.25 mol), and 50 mg of dibutyltin dilaurate (FASCAT® 4202). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 1.8 mole % FDCA, 16.1 mole % FDMME, 82.1 mole % FDME, 0.05 mole % DME. No decarboxylation products, MF and FA, were descried.

2) Dioctyltin Oxide Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of dioctyltin oxide (FASCAT® 8201). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 1.9 mole % FDCA, 22.0 mole % FDMME, 76.1 mole % FDME, 0.07 mole % DME. No decarboxylation products, MF and FA, were descried.

III. Comparative Ineffective Catalysts

A. In Methanol Solvent

1) Dibutyltin Dichloride Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of dibutyltin dichloride (FASCAT® 4201). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 0.7 mole % FDCA, 13.0 mole % FDMME, 86.3 mole % FDME, 1.4 mole % DME. No decarboxylation products, MF and FA, were descried.

2) Monobutyltin Dihydroxychloride Catalyzed Esterification of FDCA to FDME and FDMM Experimental: A 75 cc 316SS Parr vessels, each equipped with a glass enclosed magnetic stir bar, was charged with 10 g of FDCA (0.064 mol), 40 g of methanol (1.25 mol), and 50 mg of monobutyltin dihydroxyoxychloride (FASCAT® 4101). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 2.4 mole % FDCA, 17.3 mole % FDMME, 80.3 mole % FDME, 0.9 mole % DME. No decarboxylation products, MF and FA, were descried.

3) Stannous (II) Oxalate Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of stannous oxalate (FASCAT® 2001). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 2.9 mole % FDCA, 19.0 mole % FDMME, 78.1 mole % FDME, 0.04 mole % DME. No decarboxylation products, MF and FA, were descried.

4) Stannous Chloride Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of stannous chloride (FASCAT® 2004). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 3.3 mole % FDCA, 19.1 mole % FDMME, 77.6 mole % FDME, 1.2 mole % DME. No decarboxylation products, MF and FA, were descried.

5) Stannic Chloride Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of stannic chloride (FASCAT® 4400). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 1.9 mole % FDCA, 13.6 mole % FDMME, 84.5 mole % FDME, 1.7 mole % DME. No decarboxylation products, MF and FA, were descried.

6) Stannous (II) Octoate Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of stannous octoate (FASCAT® 2003). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 3.0 mole % FDCA, 18.5 mole %

FDMME, 78.5 mole % FDME, 0.03 mole % DME. No decarboxylation products, MF and FA, were descried.

7) Titanium (IV) Tetraisopropoxide Catalyzed Esterification of FDCA to FDME and FDMME Experimental: A 75 cc 316SS Parr vessels, each equipped with a glass enclosed magnetic stir bar, was charged with 10 g of FDCA (0.064 mol), 40 g of methanol (1.25 mol), and 50 mg of titanium tetraisopropoxide (TYZOR® TTIP). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 5.1 mole % FDCA, 22.2 mole % FDMME, 72.7 mole % FDME, 0.01 mole % DME. No decarboxylation products, MF and FA, were descried.

8) Titanium Tetrabutoxide Catalyzed Esterification of FDCA to FDME and FDMME Experimental: A 75 cc 316SS Parr vessels, each equipped with a glass enclosed magnetic stir bar, was charged with 10 g of FDCA (0.064 mol), 40 g of methanol (1.25 mol), and 50 mg of titanium tetrabutoxide (TYZOR® TBT). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 5.0 mole % FDCA, 22.0 mole % FDMME, 73.0 mole % FDME, 0.01 mole % DME. No decarboxylation products, MF and FA, were descried.

B. In FDME Solvent, 8 Mole Equivalents Methanol

1) Titanium Tetraisopropoxide Catalyzed Esterification of FDCA to FDME and FDMME Experimental: A 75 cc 316SS Parr vessels, each equipped with a glass enclosed magnetic stir bar, was charged with 10 g of FDCA (0.064 mol), 30 g of FDME, 16.4 g of methanol and 50 mg of titanium tetraisopropoxide (TYZOR® TTIP). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 6.4 mole % FDCA, 50.3 mole % FDMME, 43.3 mole % FDME, 0.01 mole % DME. No decarboxylation products, MF and FA, were descried.

2) Stannic Chloride Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of stannic chloride (FASCAT® 4400). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 5.8 mole % FDCA, 44.7 mole % FDMME, 49.5 mole % FDME, 0.6 mole % DME. No decarboxylation products, MF and FA, were descried.

IV. Comparative Brønsted Acids

A. Sulfuric Acid Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of sulfuric acid (Sigma Aldrich). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 0.7 mole % FDCA, 11.2 mole % FDMME, 88.1 mole % FDME, 2.5 mole % DME. No decarboxylation products, MF and FA, were descried.

B. Triflic Acid Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of triflic acid (Sigma Aldrich). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA) The compositional analysis was as follows: 0.5 mole % FDCA, 10.7 mole % FDMME, 88.8 mole % FDME, 2.6 mole % DME. No decarboxylation products, MF and FA, were descried.

C. p-Toluenesulfonic Acid Catalyzed Esterification of FDCA to FDME and FDMME

Experimental: A 75 cc 316SS Parr vessels, each equipped with a glass enclosed magnetic stir bar, was charged with 10 g of FDCA (0.064 mol), 40 g of methanol (1.25 mol), and 50 mg of p-toluenesulfonic acid (Sigma Aldrich). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 2.6 mole % FDCA, 17.1 mole % FDMME, 80.3 mole % FDME, 1.1 mole % DME. No decarboxylation products, MF and FA, were descried.

D. Phosphonic Acid

Experimental: A 75 cc 316SS Parr vessels, each equipped with a glass enclosed magnetic stir bar, was charged with 10 g of FDCA (0.064 mol), 40 g of methanol (1.25 mol), and 50 mg of phosphonic acid (Sigma Aldrich). While stirring at 875 rpm, the suspension was heated to 200° C. for 60 minutes, including a 30 minute heat up requirement. After this time, the reaction was quickly quenched by immersion of the vessel in an ice bath. The solid residual material was dried and analyzed (UPLC-PDA). The compositional analysis was as follows: 3.2 mole % FDCA, 17.9 mole % FDMME, 78.9 mole % FDME, 0.9 mole % DME. No decarboxylation products, MF and FA, were descried.

V. FDCA Esterification with Other Alcohols, Example Effectiveness of Select Catalyst Butylstannoic Acid A. FDCA Esterification with Ethanol to FDEE and FDMEE

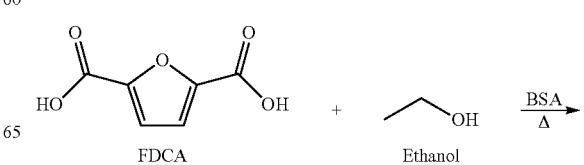

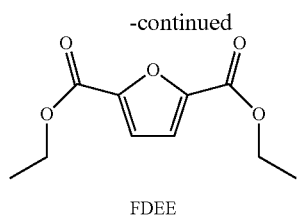

FDEE

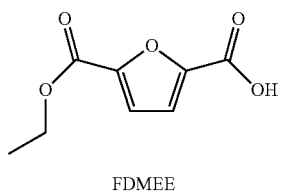

FDMEE

Experimental: A 75 cc 316SS Parr vessels, each equipped with a glass enclosed magnetic stir bar, was charged with 10 g of FDCA (0.064 mol), 40 g of ethanol and 50 mg of butylstannoic acid (FASCAT® 9100). While stirring at 875 rpm, the suspension was heated to 200° C. for 60 minutes, including a 30 minute heat up requirement. After this time, the reaction was quickly quenched by immersion of the vessel in an ice bath. The liquid residual material was dried and analyzed by H NMR (400 MHz, $d^6$-DMSO). The compositional analysis was as follows: 0.8 mole % FDCA, 15.4 mole % FDMEE, 83.8 mole % FDEE. No decarboxylation products, MF and FA, were descried.

B. FDCA Esterification with n-butanol to FDBE and FDMBE

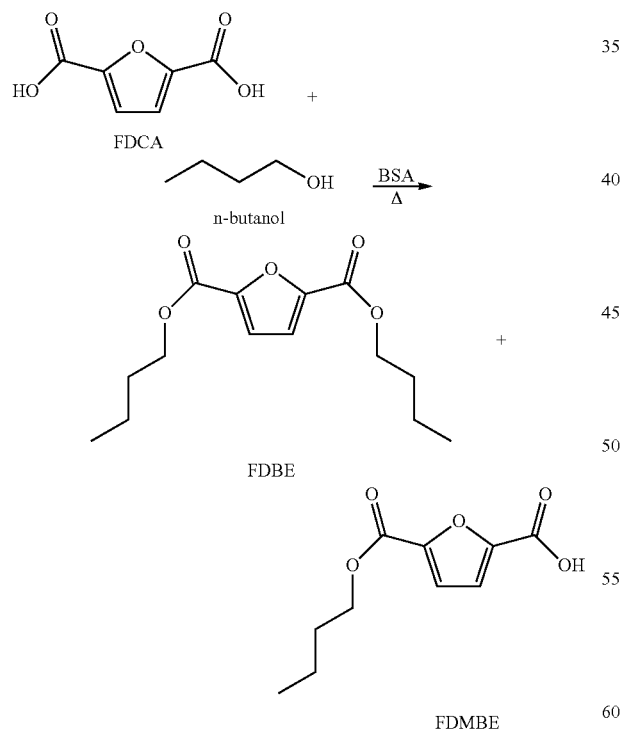

FDMBE

Experimental: A 75 cc 316SS Parr vessels, each equipped with a glass enclosed magnetic stir bar, was charged with 10 g of FDCA (0.064 mol), 40 g of n-butanol and 50 mg of butylstannoic acid (FASCAT® 9100). While stirring at 875 rpm, the suspension was heated to 200° C. for 60 minutes, including a 30 minute heat up requirement. After this time, the reaction was quickly quenched by immersion of the vessel in an ice bath. The liquid residual material was dried and analyzed by $^1$H NMR (400 MHz, $d^6$-DMSO). The compositional analysis was as follows: 0.8 mole % FDCA, 17.2 mole % FDMBE, 82.0 mole % FDBE. No decarboxylation products, MF and FA, were descried.

C. FDCA Esterification with Phenol to FDPE and FDMPE

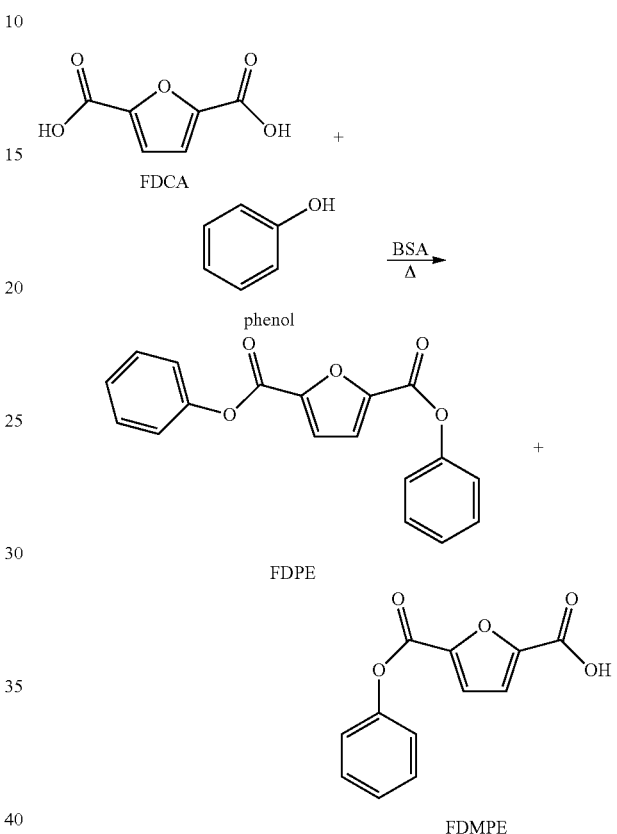

FDMPE

Experimental: A 75 cc 316SS Parr vessels, each equipped with a glass enclosed magnetic stir bar, was charged with 10 g of FDCA (0.064 mol), 40 g of phenol and 50 mg of butylstannoic acid (FASCAT® 9100). While stirring at 875 rpm, the suspension was heated to 200° C. for 60 minutes, including a 30 minute heat up requirement. After this time, the reaction was quickly quenched by immersion of the vessel in an ice bath. The liquid residual material was dried and analyzed by H NMR (400 MHz, $d^6$-DMSO). The compositional analysis was as follows: 1.2 mole % FDCA, 15.5 mole % FDMPE, 82.1 mole % FDPE. No decarboxylation products, MF and FA, were descried.

D. FDCA Esterification with Benzyl Alcohol to FDBzE and FDMBzE

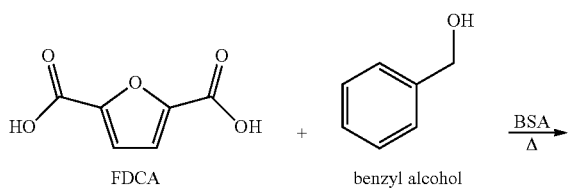

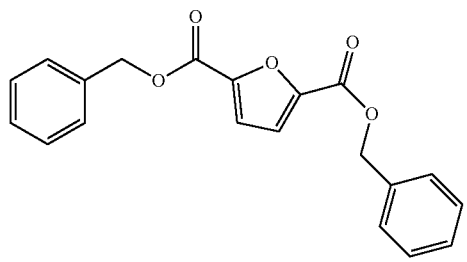

FDBzE

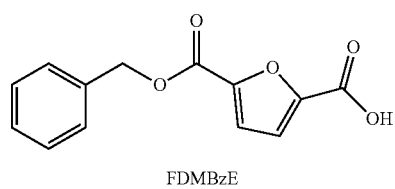

FDMBzE

Experimental: A 75 cc 316SS Parr vessels, each equipped with a glass enclosed magnetic stir bar, was charged with 10 g of FDCA (0.064 mol), 40 g of benzyl alcohol and 50 mg of butylstannoic acid (FASCAT® 9100). While stirring at 875 rpm, the suspension was heated to 200° C. for 60 minutes, including a 30 minute heat up requirement. After this time, the reaction was quickly quenched by immersion of the vessel in an ice bath. The liquid residual material was dried and analyzed by $^1$H NMR (400 MHz, d$^6$-DMSO). The compositional analysis was as follows: 1.9 mole % FDCA, 21.1 mole % FDMBzE, 73.0 mole % FDBzE. No decarboxylation products, MF and FA, were descried.

E. FDCA Esterification with 2-ethylhexanol to FD(2EH) and FDM(2EH).

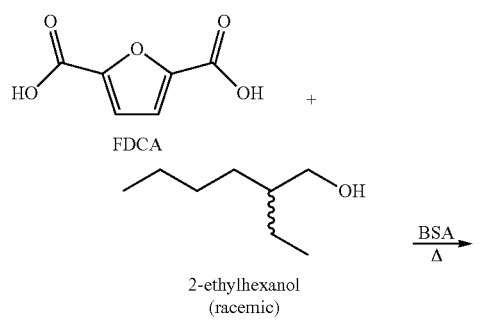

FD (2EH)
(Diastereomers)

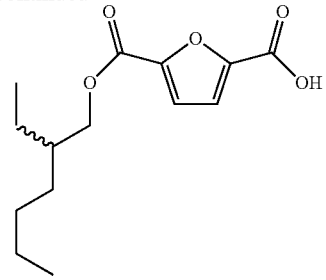

FDM (2EH)
(Enantiomers)

Experimental: A 75 cc 316SS Parr vessels, each equipped with a glass enclosed magnetic stir bar, was charged with 10 g of FDCA (0.064 mol), 40 g of 2-ethylhexanol and 50 mg of butylstannoic acid (FASCAT® 9100). While stirring at 875 rpm, the suspension was heated to 200° C. for 60 minutes, including a 30 minute heat up requirement. After this time, the reaction was quickly quenched by immersion of the vessel in an ice bath. The liquid residual material was dried and analyzed by $^1$H NMR (400 MHz, d$^6$-DMSO). The compositional analysis was as follows: 3.2 mole % FDCA, 21.1 mole % FDM(2EH), 75.7 mole % FD(2EH). No decarboxylation products, MF and FA, were descried.

F. FDCA Esterification with 5-hydroxymethyl-2-furfural (HMF) to FDCA-HMF Monoester and FDCA-HMF Diester.

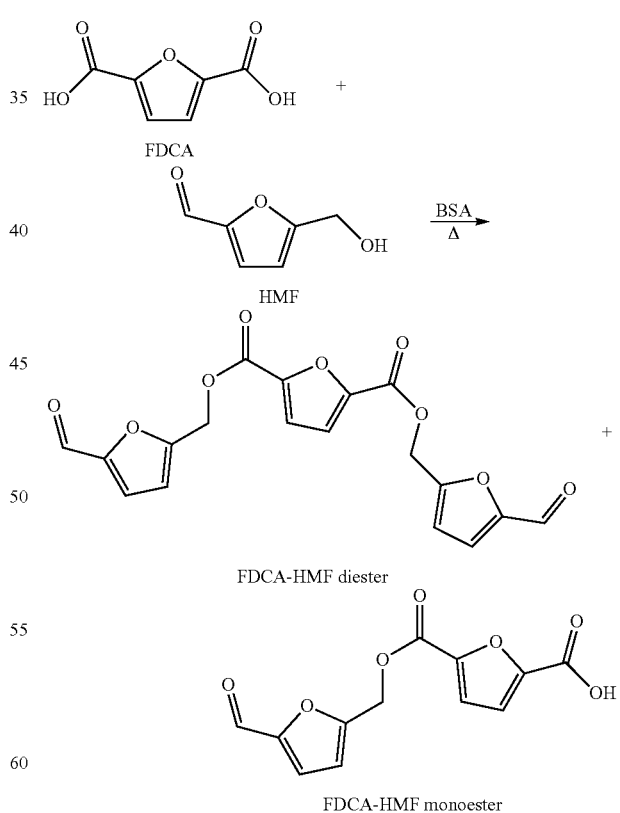

Experimental: A 75 cc 316SS Parr vessels, each equipped with a glass enclosed magnetic stir bar, was charged with 10 g of FDCA (0.064 mol), 40 g of HMF and 50 mg of butylstannoic acid (FASCAT® 9100). While stirring at 875 rpm, the suspension was heated to 200° C. for 60 minutes, including a 30 minute heat up requirement. After this time, the reaction was quickly quenched by immersion of the vessel in an ice bath. The liquid residual material was dried and analyzed by $^1$H NMR (400 MHz, d$^6$-DMSO). The compositional analysis was as follows: 2.1 mole % FDCA, 26.0 mole FDCA-HMF monoester, 68.7 mole % FDCA-HMF diester. No decarboxylation products, MF and FA, were descried.

In another example, one can compare batch esterification of terephthalic acid (TPA) and adipic acid (AA), two commodity non-furanic diacids, using methanol as catalyzed using tin (II) acetate, tin (II) octoate, tin (II) glucarate, respectively. Reaction conditions: 17 wt. % TPA or AA in methanol, 0.5 mole % catalyst, 200° C., 30 min (30 min heat up); 75 cc autoclave with magnetic stirring. Samples are withdrawn, dried, and analyzed by UPLC-UV (TPA) or $^1$H NMR (AA). As summarized in Table 5, tin acetate demonstrated superior activity in both situations. With tin acetate or tin glucarate catalysts one can achieve greater than 85 wt. % conversion of TPA to the dimethylterephthalate ester. Between the two species, the tin acetate catalyst performs moderately better.

TABLE 5

TPA esterification:

| Catalyst | TPA (wt. %) | MMT (wt. %) | DMT (wt. %) |
| --- | --- | --- | --- |
| Tin Acetate | 0.4 | 10.7 | 88.9 |
| Tin Glucarate | 0.4 | 13.1 | 86.4 |
| Tin Octoate | 3.8 | 36.3 | 59.9 |

MMT = monomethyl terephthalic acid;
DMT = dimethylterephthalate

Similarly, NMR analysis of AA esterification reveals that the tin acetate catalyst can achieve a significant advantage over the other two catalyst species. Tin acetate achieves 96 mole % AA conversion to mono and dimethyl esters in comparison to tin glucarate, which exhibits 70 mole % AA conversion to mono and dimethyl esters, and tin octoate, which produces 69 mole % AA conversion to mono and dimethyl esters.

In addition to the utility of the Sn (IV) catalysts, the foregoing experiments suggest that tin (II) acetate salt can also be a superior or beneficial catalyst not only for FDCA esterification as well as certain diacids. The effective tin catalysts comprise the organotins, which by definition, have at least one carbon-tin covalent bond, and are in their +4 oxidation state. Tin (II) salts, in general, were moderately effective as catalysts in esterification processes; however, tin (II) acetate was a surprising exception, which furnished high yields of diesters and conversed diacids in the diesterification examples provided. It is unclear whether tin (IV) acetate would afford any improvements over tin (II) acetate, as this species is not an organotin. Furthermore, one would unlikely utilized tin (IV) acetate, owing to its exorbitant cost relative to analogous organotins.

Although the present invention has been described generally and by way of examples, it is understood by those persons skilled in the art that the invention is not necessarily limited to the embodiments specifically disclosed, and that modifications and variations can be made without departing from the spirit and scope of the invention. Thus, unless changes otherwise depart from the scope of the invention as defined by the following claims, they should be construed as included herein.

We claim:

1. A process of preparing esters of furan-2,5-dicarboxylic acid (FDCA) comprising: reacting FDCA with at least an alcohol or a mixture of different alcohols in either an alcohol or diester solvent matrix in the presence of a homogeneous organotin catalyst at a loading level of up to 10 mol. % for a reaction time and temperature sufficient to esterify said FDCA and produce a di-ester species at a FDCA conversion of at least 80 mol. %, and a di-ester yield of at least 5 mol. % greater than a comparable amount of Brønsted acid catalyst.

2. The process according to claim 1, wherein said alcohol is either an aliphatic, having $C_1$-$C_{20}$ chain, or aromatic alcohol species.

3. The process according to claim 2, wherein said alcohol is selected from the group consisting of: methanol, ethanol, propanol, isopropanol, n-butanol, sec-butanol, isobutanol, n-pentanol, 2-pentanol, 3-pentanol, n-hexanol, isohexanol, 2-ethylhexanol, heptanol, octanol, nonanol, decanol, phenol, benzyl alcohol, and 5-hydroxymethylfurfural.

4. The process according to claim 1, wherein either said alcohol solvent matrix or di-ester matrix is sufficient to dissolve said FDCA, at about 50 wt. % to about 99 wt. % relative to an amount of FDCA.

5. The process according to claim 4, wherein either said alcohol solvent matrix or di-ester solvent matrix is at about 75 wt. % to about 97 wt. % relative to an amount of FDCA.

6. The process according to claim 1, wherein a tin ion of said organotin catalyst is Sn (IV).

7. The process according to claim 1, wherein said organotin catalyst has at least one tin-carbon covalent bond.

8. The process according to claim 1, wherein said organotin catalyst is selected from the group consisting of: butylstannoic acid, dibutyltin oxide, dibutyltin diacetate, stannous (II) acetate, butyltin tris 2-ethylhexanoate, dibutyltin maleate, dibutyltin dilaurate, dioctyltin oxide, dibutyltin bis(1-thioglyceride), dibutyltin dichloride, and monobutyltin dihydroxychloride.

9. The process according to claim 8, wherein said organotin catalyst can be selected from: butylstannoic acid, dibutyltin oxide, dibutyltin diacetate, butyltin tris 2-ethylhexanoate, stannous (II) acetate.

10. The process according to claim 1, wherein said process using a homogeneous organotin catalyst achieves a FDCA conversion of at least 5% greater, or a mono- or di-ester yield of at least 10 mol. % greater than a process reacted using a comparable amount of Brønsted acid catalyst.

11. The process according to claim 1, wherein said loading level of organotin catalyst is in a range from about 0.01 mol. % to about 5 mol. %.

12. The process according to claim 11, wherein said loading level of said organotin catalysts is in a range from about 0.01 mol. % to about 1.5 mol. %.

13. The process according to claim 1, wherein said reaction time is up to about 12 hours.

14. The process according to claim 13, wherein said reaction time is in a range from about 10 minutes to about 8 hours.

15. The process according to claim 1, wherein said reaction temperature is in a range from about 80° C. to about 275° C.

16. The process according to claim 15, wherein said reaction temperature is in a range from about 110° C. to about 250° C.

17. The process according to claim 1, wherein said FDCA conversion is at least 85 mol. % to a mono- or di-ester.

18. The process according to claim 1, wherein mono-ester includes:

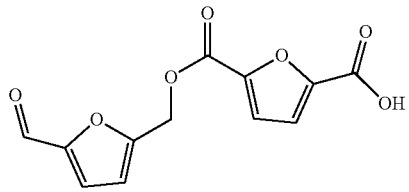

5-(((5-formylfuran-2-yl)methoxy)carbonyl)furan-2-carboxylic acid (FDCA-HMF)

and

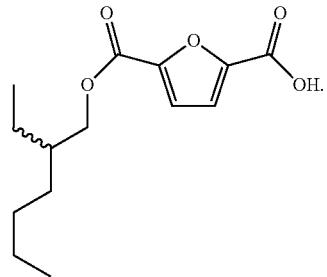

5-(((2-ethylhexyl)oxy)carbonyl)furan-2-carboxylic acid (FDCA-2EH).

19. The process according to claim 1, wherein said yield of diester is at least 70 mol. %.

20. The process according to claim 19, wherein said yield of diester is about 80 mol. % to about 95 mol. %.

21. The process according to claim 1, wherein said di-ester includes:

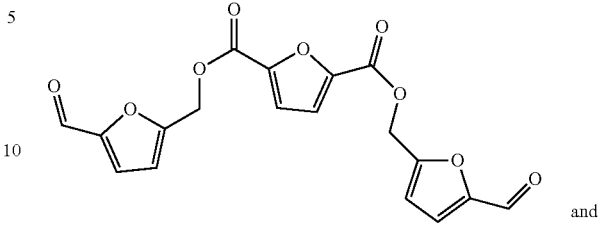

bis((5-formylfuran-2-yl)methyl)furan-2,5-dicrboxylate (FDCA-HMF)

and

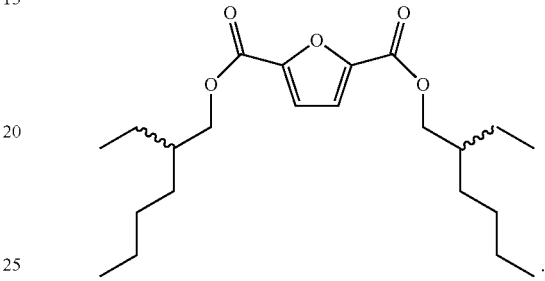

bis(2-ethylhexyl)furan-2,5-dicarboxylate (FDCA di(2EH)).

22. The process according to claim 18, wherein said FDCA conversion is at least about 90 mol. % to about 99 mol. %.

* * * * *